United States Patent [19]

Nakao et al.

[11] 4,003,901
[45] Jan. 18, 1977

[54] NITROSOUREA DERIVATIVE

[75] Inventors: Hideo Nakao; Masao Arakawa; Masami Fukushima, all of Tokyo, Japan

[73] Assignee: Sankyo Company Limited, Tokyo, Japan

[22] Filed: Nov. 25, 1974

[21] Appl. No.: 527,017

Related U.S. Application Data

[63] Continuation of Ser. No. 307,042, Nov. 16, 1972, abandoned.

[30] Foreign Application Priority Data

Nov. 20, 1971 Japan ............................. 46-93485
Dec. 4, 1971 Japan ............................. 46-98034
July 26, 1972 Japan ............................. 47-74782

[52] U.S. Cl. .................. 260/256.4 N; 260/239 BC; 260/250 R; 260/250 BN; 260/256.4 Q; 260/256.4 R; 260/288 R; 260/293.87; 260/295 E; 260/302 F; 260/302 A; 260/307 D; 260/307 H; 260/307 R; 260/309.6; 260/310 R

[51] Int. Cl.$^2$ ....................................... C07D 239/42
[58] Field of Search ............................ 260/256.4 N

[56] References Cited

OTHER PUBLICATIONS

Smith, P. A. S., "Open Chain Nitrogen Compounds," vol. 1, 1965, W. A. Benjamin, Inc. pp. 272–273.
Johnson, et al. (I), "J. Med. Chem." vol. 6, 1963, pp. 669–675.
Johnson, et al. (II), "J. Med. Chem.," vol. 9, 1966, pp. 892, 898–899, 907 and 909–910.

Primary Examiner—Richard J. Gallagher
Assistant Examiner—James H. Turnipseed
Attorney, Agent, or Firm—Toren, McGeady and Stanger

[57] ABSTRACT

Nitrosourea derivatives represented by the formula

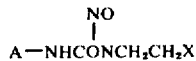

A—NHCONCH$_2$CH$_2$X   (I)

wherein
A represents a group of the formula B—Y— in which B is an unsaturated 5- or 6-membered heterocyclic group which has the as hetero atom at least one nitrogen atom, an unsaturated 9-membered heterocyclic group which has as the hetero atom at least one nitrogen atom and a bicyclic fused ring or an unsaturated 10-membered heterocyclic group which has as the hetero atom at least one nitrogen atom and a bicyclic fused ring, the heterocyclic groups optionally having alkyl, alkoxy, hydroxyl, amino, hydroxyalkyl or halogen as ring substituent and Y represents a group of the formula —(CH$_2$)$_m$— in which $m$ is an integer of 1 or 2, the group optionally having alkyl as a substituent;

a group of the formula

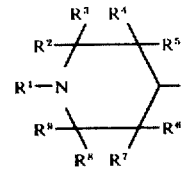

in which R$^1$, R$^2$, R$^3$, R$^4$, R$^5$, R$^6$, R$^7$, R$^8$ and R$^9$ may be the same or different and each represents a hydrogen atom or an alkyl group; or a group of the formula

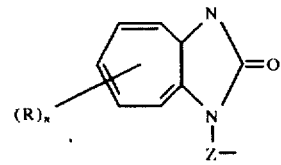

in which R's may be the same or different and each represents a halogen atom or an alkyl group, $n$ is an integer of 0 to 3 inclusive and Z is an ethylene group which may be substituted with alkyl; and X represents a halogen atom and acid addition salts thereof. The Compounds of the present invention are prepared from the corresponding 2-halogeno-ethylurea derivatives by means of conventional nitrosation procedures and useful as an antileukemic drug for various types of leukemia.

1 Claim, No Drawings

NITROSOUREA DERIVATIVE

This is a continuation of application Ser. No. 307,042, filed Nov. 16, 1972 now abandoned.

This invention relates to a new class of nitrosourea derivatives and a process for preparing the same.

More particularly, this invention is concerned with a nitrosourea derivative having the formula

wherein
A represents a group of the formula B—Y—
in which
B is an unsaturated 5- or 6-membered heterocyclic group which has as hetero atom at least one nitrogen atom, an unsaturated 9-membered heterocyclic group which has as hetero atom at least one nitrogen atom and a bicyclic fused ring or an unsaturated 10-membered heterocyclic group which has as hetero atom at least one nitrogen atom and a bicyclic fused ring, the heterocyclic groups optionally having alkyl, alkoxy, hydroxyl, amino, hydroxyalkyl or halogen as ring substituent and
Y represents a group of the formula —(CH$_2$)$_m$— in which $m$ is an integer of 1 or 2, the group optionally having alkyl as substituent;
a group of the formula

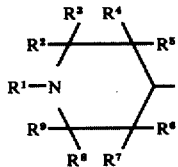

in which R$^1$, R$^2$, R$^3$, R$^4$, R$^5$, R$^6$, R$^7$, R$^8$ and R$^9$ may be the same or different and each represents hydrogen atom or an alkyl group; or
a group of the formula

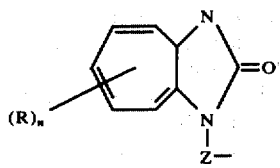

in which R's may be the same or different and each represents a halogen atom or an alkyl group, $n$ is an integer of 0 to 3 inclusive and Z is an ethylene group which may be substituted with alkyl; and
X represents a halogen atom and an acid addition salt thereof.

This invention is also concerned with a process for the preparation of the nitrosourea derivative (I).

In the above formula (I), the group B may be illustratively exemplified by the following heterocyclic groups: pyridyl, pyrimidyl, N-oxypyridyl, pyrazinyl, pyridazinyl, thiazolyl isothiazolyl, oxazolyl, isoxazolyl, imidazolyl, pyrazolyl; benzimidazolyl, benzothiazolyl, benzoxazolyl; and quinolyl, quinazolinyl. The group Y may be illustratively exemplified by methylene, ethylene and propylene. The substituents of the heterocyclic group B are intended to embrace, preferably, alkyl groups of 1 to 3 carbon atoms, e.g., methyl, ethyl, propyl; alkoxy groups of 1 to 3 carbon atoms, e.g., methoxy, ethoxy, propoxy; hydroxyl; amino; hydroxyalkyl groups of 1 to 3 carbon atoms, e.g., hydroxymethyl, 2-hydroxyethyl, 3-hydroxypropyl; and halogen atoms, e.g., chlorine, bromine, fluorine, iodine. The groups R$^1$ through R$^9$ may be individually and illustratively exemplified by hydrogen atom and an alkyl group, preferably, of 1 to 3 carbon atoms, e.g., methyl, ethyl, propyl. The group R may be exemplified by halogen atom, e.g., chlorine, bromine, fluorine, iodine and an alkyl group, preferably, of 1 to 3 carbon atoms, e.g., methyl, ethyl, propyl. The group Z may be exemplified by ethylene and substituted ethylene having alkyl, preferably, of 1 to 3 carbon atoms, e.g., propylene, 1-ethylethylene, 1-propylethylene.

Heretofore, J. A. Montogomery et al. have reported some related nitrosourea derivatives having antileukemic activity in the Journal of Medicinal Chemistry, 6, 669, (1963) and ibid, 9, 892, (1966). For example, 1,3-bis-(2-chloroethyl)-1-nitrosourea (referred to as BCNU) and 1-(2-chloroethyl)-3-cyclohexyl-1-nitrosourea (referred to as CCNU) have been proposed to show antileukemic activity. However, these urea derivatives are found to have serious drawbacks particularly, in that they are insoluble or extremely sparingly soluble in water, which leads to difficulty in preparing injectable solutions when they are to be applied for therapeutic purposes.

As a result of our extensive studies to improve the above-depicted drawback and find out more effective and easily applicable nitrosourea derivatives, it has been found that the new nitrosourea derivatives of the formula (I) possess potent antileukemic activity against various types and severities of leukemia, especially lymphoid leukemia and, unexpectedly, they also have a high solubility in water and thus they are highly useful as an antileukemic drug for the remission and treatment of leukemia in view of their pharmacological and physicochemical properties.

It is, accordingly, a principal object of this invention to provide the new nitrosourea derivative (I) which can be more practically utilized for the remission and treatment of leukemia.

Another object of this invention is to provide a chemical process for the preparation of such useful nitrosourea derivatives (I).

Other objects and advantages will be apparent from the following description.

So far as the results are concerned in animal tests employing lymphoid leukemia L 1210 in mice, substantially according to the teachings from the protocols of Cancer Chemotherapy National Service Center in National Institute of Health, Bethesda 14, Maryland, U.S.A. and in other animal tests employing Ehrlich ascites-tumor, Sarcoma 180, Adenocarcinoma 755 and the like, the nitrosourea derivatives (I) have been proved to possess an excellent antitumor activity, resulting in a prolonged survival of test animals.

The nitrosourea derivatives (I) of this invention may be usually administered through oral or parenteral route, preferably by intravenous injection. The active nitrosourea derivatives (I) of this invention may be employed for the clinical application in various types of unit dosage forms, but is practical and preferable to employ a single dose of the nitrosourea derivative (I) aseptically dissolved into a suitable physiologically acceptable solvent, e.g., physiological saline thereby to form a liquid preparation for parenteral administration. However, they may be administered via oral route in the form of, for example, tablets, capsules, suspensions, syrups and the like. Single daily dose of the nitrosourea derivative (I) of this invention may be usually within the range of about 5 mg. to about 100 mg. per adult. However, administration and dosage may be, of course, varied depending upon the types and severities of leukemia, the body weight and age of the patients and other factors and it is to be understood that administration should be carefully made upon proper consideration of the types and severities of leukemia, possible side effects, toxicity and other factors.

In one aspect of this invention, there are provided a new class of the nitrosourea derivatives (I) and acid addition salts thereof. Briefly speaking, the nitrosourea derivatives (I) of this invention may include the following three groups:

A nitrosourea derivative having the formula

(I-a)

wherein B, X and Y are as defined above;
a nitrosourea derivative having the formula

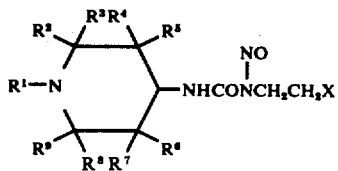
(I-b)

wherein $R^1$, $R^2$, $R^3$, $R^4$, $R^5$, $R^6$, $R^7$, $R^8$, $R^9$ and X are as defined above; and
a nitrosourea derivative having the formula

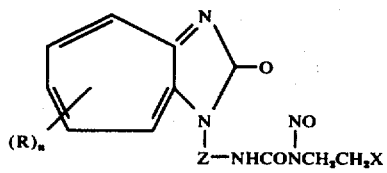
(I-c)

wherein R, n, X and Z are as defined above.
Representative of the nitrosourea derivatives (I) of this invention are the following:

| Compound No. | Chemical Name |
| --- | --- |
| 1. | 1-(2-chloroethyl)-1-nitroso-3-[(4-pyridyl)methyl]urea |
| 2. | 1-(2-chloroethyl)-1-nitroso-3-[(3-pyridyl)methyl]urea |
| 3. | 1-(2-chloroethyl)-1-nitroso-3-[(2-pyridyl)methyl]urea |
| 4. | 1-(2-chloroethyl)-1-nitroso-3-[(2-methyl-3-hydroxy-5-hydroxymethyl-pyridine-4-yl)methyl]urea |
| 5. | 1-(2-chloroethyl)-1-nitroso-3-[2-(2-pyridyl)ethyl]urea |
| 6. | 1-(2-chloroethyl)-1-nitroso-3-[(2-methyl-4-aminopyrimidine-5-yl)methyl]-urea |
| 7. | 4-[3-(2-chloroethyl)-3-nitrosoureido]-1-methylpiperidine |
| 8. | 4-[3-(2-chloroethyl)-3-nitrosoureido]-2,2,6,6-tetramethylpiperidine |

-continued

| Compound No. | Chemical Name |
| --- | --- |
| 9. | 1-{2-[3-(2-chloroethyl)-3-nitrosoureido]-ethyl}-cycloheptimidazole-2(1H)-one |
| 10. | 6-chloro-1-{2-[3-(2-chloroethyl)-3-nitrosoureido]ethyl}-cycloheptimidazole-2-(1H)-one |
| 11. | 5-isopropyl-1-{2-[3-(2-chloroethyl)-3-nitrosoureido]ethyl}-cycloheptimidazole-2(1H)-one |
| 12. | 2-[3-(2-chloroethyl)-3-nitrosoureido]-methylpyrazine |
| 13. | 3-[3-(2-chloroethyl)-3-nitrosoureido]-methylpyridazine |
| 14. | 2-[3-(2-chloroethyl)-3-nitrosoureido]methyloxazole |
| 15. | 3-[3-(2-chloroethyl)-3-nitrosoureido]methylisoxazole |
| 16. | 2-[3-(2-chloroethyl)-3-nitrosoureido]methyl-1-methylimidazole |
| 17. | 3-[3-(2-chloroethyl)-3-nitrosoureido]methyl-1-methylpyrazole |
| 18. | 3-[3-(2-chloroethyl)-3-nitrosoureido]methylisothiazole |
| 19. | 4-[3-(2-chloroethyl)-3-nitrosoureido]methylpyridine N-oxide |
| 20. | 2-[3-(2-chloroethyl)-3-nitrosoureido]methylbenzothiazole |
| 21. | 2-[3-(2-chloroethyl)-3-nitrosoureido]methylbenzoxazole |
| 22. | 2-[3-(2-chloroethyl)-3-nitrosoureido]methylquinazoline |
| 23. | 2-[3-(2-chloroethyl)-3-nitrosoureido]methyl-1-methylbenzimidazole |
| 24. | 1-{2-[3-(2-chloroethyl)-3-nitrosoureido]ethyl}-benzimidazole |
| 25. | 1-{2-[3-(2-chloroethyl)-3-nitrosoureido]ethyl-propyl}benzimidazole |
| 26. | 2-[3-(2-chloroethyl)-3-nitrosoureidomethyl]-quinoline |
| 27. | 2-[3-(2-chloroethyl)-3-nitrosoureido]methylthiazole. |

In view of their pharmacological and physico-chemical properties of the nitrosourea derivatives of the above formulae (I-a), (I-b) and (I-c), the following nitrosourea derivatives are preferred:

The nitrosourea derivatives of the formula (I-a) wherein B is pyridyl group, pyrimidyl group, thiazolyl group, benzimidazolyl group or quinolyl group, Y is methylene group or ethylene group and X is chlorine atom; the nitrosourea derivatives of the formula (I-b) wherein $R^1$ is hydrogen atom or an alkyl group, $R^2$, $R^3$, $R^8$ and $R^9$ are individually hydrogen atom or an alkyl group, $R^4$, $R^5$, $R^6$ and $R^7$ are individually hydrogen atom and X is chlorine atom; and the nitrosourea derivatives of the formula (I-c) wherein R is a halogen atom or an alkyl group, n is an integer of 0 or 1 and Z is ethylene group.

A more preferable group of the nitrosourea derivatives of the formula (I) involves the following compounds:

1-{2-[3-(2-chloroethyl)-3-nitrosoureido]ethyl}-cycloheptimidazole-2(1H)-one;

1-(2-chloroethyl)-1-nitroso-3-[(3-pyridyl)methyl]urea;

1-(2-chloroethyl)-1-nitroso-3-[(4-pyridyl)methyl]urea;

4-[3-(2-chloroethyl)-3-nitrosoureido]-2,2,6,6-tetramethylpiperidine; and 1-(2-chloroethyl)-1-nitroso-3-[(2-methyl-4-aminopyrimidine-5-yl)methyl]urea.

In another aspect of this invention, there is provided a process for the preparation of the nitrosourea derivative of the formula (I). The process of this invention comprises subjecting a 2-halogenoethylurea derivative having the formula

wherein A and X are as defined above to nitrosation.

In carrying out the process of this invention, the reaction can be easily effected by the use of a nitrosating agent according to a procedure commonly employed for nitrosation in the art. As the nitrosating agent which may be employed in the reaction of this invention may be any of those agents that could be utilized for nitrosation of the N atom and would not adversely affect the reaction proceeding and the final product. For instance, this may be accomplished by reaction with a metal salt of nitrous acid or an alkyl nitrite in the presence of an inorganic or organic acid. As the metal salt of nitrous acid may be employed without critical limitation any of ordinarily available metal salts of nitrous acid, e.g., sodium, potassium, lithium, thallium, silver, barium calcium, magnesium, nickel, copper and cadmium nitrites. As the alkyl nitrate may be employed without critical limitation any of lower alkyl nitrites, e.g., methyl, ethyl, propyl, butyl and amyl nitrites. As the inorganic or organic acid may be employed any of inorganic and organic acids, e.g., hydrochloric, sulfuric, nitric, formic, acetic and propionic acids.

The reaction can be usually effected in the presence or absence of a solvent. As the solvent may be employed without critical limitation any of those solvents that would be inert to the reaction, preferably such solvents as water; alcohols, e.g., methanol and ethanol; ethers, e.g., diethyl ether, dioxane and tetrahydrofuran; and a mixture thereof. Where the metal salt of nitrous acid is employed, water and aqueous organic solvents composed of water and a water-miscible organic solvent are preferred. Alternatively, where the alkyl nitrite and a water-immiscible organic solvent, e.g., diethyl ether are employed, nitrosation is accomplished by direct introduction of gaseous hydrogen halide, e.g., hydrogen chloride into the reaction system.

The reaction temperature is not critical, but the reaction can be usually and preferably effected at a temperature ranging from room temperature to a lower one.

The reaction period of time may vary depending on the type of the nitrosating agent employed and the reaction temperature applied, but it may usually fall within the range from about 30 minutes to about 5 hours.

After completion of nitrosation, the desired product may be readily recovered from the reaction mixture by a conventional method. For instance, where the desired product is separated out in situ as crystalline mass, the mass is recovered by filtration. Alternatively, where the desired product is dissolved into the reaction mixture, the reaction mixture is made alkaline by the addition of a basic substance, such as, sodium carbonate and sodium bicarbonate, whereupon crystalline mass is separated out in situ and then recovered by filtration. If the separated product is oily, the reaction mixture is extracted with a suitable organic solvent, such as, methylene chloride and chloroform and the solvent is distilled off from the extract to recover the desired product.

The product so obtained may be, if necessary, further purified by a conventional means, e.g., recrystallization, column chromatography, thin layer chromatography and the like.

The starting materials of the formula (II) may be utilized in the form of either a free base or an acid addition salt thereof in the process of this invention. Examples of the acid addition salts of the starting material include those acid addition salts with inorganic acids, e.g., hydrochloric, sulfuric, nitric and phosphoric acids, and organic acids, e.g., acetic, maleic, citric, tartaric, oxalic and succinic acids.

The starting materials of the formula (II) which may be employed in this invention are all new compounds and can be easily prepared, for instance, by reacting a compound having the formula

wherein A is as defined above with a 2-halogenoethyl isocyanate.

As explained hereinabove, the pharmaceutically acceptable acid addition salts of the nitrosourea derivatives (I) are also contemplated to fall within the scope of this invention and these salts may be advantageously prepared by reaction with an inorganic or organic acid according to usual procedures. Examples of such acids which may be employed for the formation of the corresponding acid addition salts are hydrochloric, hydrobromic, hydroiodic, sulfuric, nitric and phosphoric acids; and acetic, maleic, oxalic, citric, tartaric and succinic acids.

Those acid addition salts with hydrochloric acid are preferable.

The following examples and referential examples are given solely for the purpose of illustrating of this invention.

EXAMPLE 1

1-(2-Chloroethyl)-1-nitroso-3-[(4-pyridyl)methyl-]urea

To a solution of 6.3 g. of 1-(2-chloroethyl)-3-[(4-pyridyl)methyl]urea in 63 ml. of 5% hydrochloric acid was added gradually 3.2 g. of sodium nitrite while stirring at 0° – 10° C. After completion of the addition, the resulting mixture was stirred at a temperature below 10° C. for additional 1 hour.

After completion of the reaction, the reaction mixture was made weakly alkaline by the addition of sodium carbonate, whereupon crystalline substances were separated out in situ. The substances thus separated were recovered by filtration, washed with water and then dried to give 6 g. of the crude desired product. The product was dissolved in 45 ml. of chloroform at room temperature and to the resulting solution was added 90 ml. of ether. The resulting mixture was allowed to stand at room temperature for a while, whereupon crystalline substances were separated out. The crystalline substances were recovered by filtration and dried to give the pure desired product with pale yellow colors. m.p. 96° C.

Analysis for $C_9H_{11}N_4O_2Cl$: Calculated: C; 44.54; H, 4.57; N, 23.09. Found: C; 44.86; H, 4.58; N, 23.10.

In 40 ml. of ethanol was dissolved 1 g. of the product as obtained above and to the solution was added 4 ml. of 25% ethanolic hydrogen chloride, whereupon the hydrochloride of the above product was formed. The salt was recovered by filtration, washed with ethanol and dried to give 1 g. of the hydrochloride of the desired product having a decomposition point of 148° C.

Analysis for $C_9H_{12}N_4O_2Cl_2$: Calculated: C, 38.72; H, 4.33; N, 20.07. Found: C, 38.48; H, 4.18; N, 19.96.

EXAMPLE 2

1-(2-Chloroethyl)-1-nitroso-3-[(3-pyridyl)methyl]urea

The same reaction procedure as shown in the above Example 1 was repeated except that 7 g. of 1-(2-chloroethyl)-3-[(3-pyridyl)methyl]urea and 70 ml. of 5% hydrochloric acid were employed instead of the 1-(2-chloroethyl-3-[(4-pyridyl)-methyl]urea and 63 ml. of the acid, respectively.

After completion of the reaction, the reaction mixture was made alkaline by the addition of sodium carbonate to separate oily substances.

The reaction mixture was extracted with chloroform and the extract concentrated under reduced pressure to give solid residue. The residue was dissolved in 20 ml of chloroform and the resulting solution was added 40 ml. of ether. The resulting mixture was allowed to stand at room temperature, whereupon crystalline substances were separated out. The substances were recovered by filtration and dried to give 3 g. of the pale yellow colored desired product having a melting point of 87° C.

Analysis for $C_9H_{11}N_4O_2Cl$: Calculated: C, 44.54; H, 4.57; N, 23.09. Found: C, 44.25; H, 4.59; N, 23.28.

One gram of the product as obtained above was treated in the same manner as shown in the above Example 1 to give 1 g. of the hydrochloride of the desired product having a decomposition point of 138° C.

Analysis for $C_9H_{12}N_4O_2Cl_2$: Calculated: C, 38.72; H, 4.33; N, 20.07. Found: C, 38.29; H, 4.19; N, 20.01.

EXAMPLE 3

1-(2-Chloroethyl)-1-nitroso-3-[(2-pyridyl)methyl]urea

To a solution of 1 g. of 1-(2-chloroethyl)-3-[(2-pyridyl)methyl]urea in 10 ml. of 5% hydrochloric acid was added gradually 0.5 g. of sodium nitrite while stirring under ice-cooling. Thereafter, the reaction was effected in the same manner as shown in the above Example 1.

After completion of the reaction, the reaction mixture mixture was made alkaline by the addition of sodium carbonate, whereupon crystalline substances were separated out in situ. The crystalline substances were recovered by filtration, washed with water and then dissolved in a small amount of chloroform at room temperature followed by filtration. The filtrate was worked with cyclohexane to separate crystalline substances, which were then recovered by filtration and dried to give 0.6 g. of the pure desired product having slightly yellowish color and a melting point of 70° C.

Analysis for $C_9H_{11}N_4O_2Cl$: Calculated: C, 44.54; H, 4.57; N, 23.09; Cl, 14.61. Found: C, 44.89; H, 4.61; N, 22.60; Cl, 14.61.

EXAMPLE 4

1-(2-Chloroethyl)-1-nitroso-3-[(2-methyl-3-hydroxy-5-hydroxymethylpyridine-4-yl)methyl]-urea.hydrochloride To a solution of 1 g. of 1-(2-chloroethyl)-3-[(2-methyl-3-hydroxy-5-hydroxymethylpyridine-4-yl)methyl]urea.hydrochloride in 10 ml. of 5% hydrochloric acid was added gradually 0.4 g. of sodium nitrite at 0° – 5° C. while stirring. After completion of the addition, the reaction mixture was stirred at 0° – 5° C. for additional 1.5 hours. The crystalline substances separated in situ during the stirring were recovered by filtration and recrystallized from 8 ml. of ethanol to give 0.1 g. of the pure desired product having pale yellow color and a decomposition point of 171° C.

Analysis for $C_{11}H_{16}N_4O_4Cl_2$: Calculated: C, 38.95; H, 4.76; N, 16.52. Found: C, 39.19; H, 4.88; N, 16.38.

EXAMPLE 5

1-(2-Chloroethyl)-1-nitroso-3-[2-(2-pyridyl)ethyl]urea

To a solution of 1 g. of 1-(2-chloroethyl)-3-[2-(2-pyridyl)ethyl]urea in 10 ml. of 10% hydrochloric acid was added gradually 1.3 g. of sodium nitrite while stirring under ice-cooling. After completion of the addition, the reaction mixture was stirred under ice-cooling for additional 2 hours.

After completion of the reaction, the reaction mixture was made alkaline by the addition of sodium carbonate to separate oily substances in situ. The reaction mixture extracted with chloroform, the extract was washed with water and dried over anhydrous sodium sulfate. The dried extract was concentrated under reduced pressure to yield oily residue. The residue was subjected to column chromatography on 20 g. of silica gel and elution was effected by the use of methylene chloride. The solvent was distilled off from the eluate to give 380 mg. of the oily desired product having slightly yellowish color.

Analysis for $C_{10}H_{13}N_4O_2Cl$: Calculated: C, 46.79; H, 5.10; N, 21.38. Found: C, 46.15; H, 5.21; N, 21.22.

EXAMPLE 6

1-(2-Chloroethyl)-1-nitroso-3-[(2-methyl-4-aminopyrimidine-5-yl)methyl]urea

To a solution of 450 mg. of 1-(2-chloroethyl)-3-[(2-methyl-4-aminopyrimidine-5-yl)methyl]urea in 8 ml. of 5% hydrochloric acid was added 0.4 g. of sodium nitrite at 0° – 5° C. while stirring. After completion of the addition, the reaction mixture was stirred at 0° – 10° C. for additional 1.5 hours.

After completion of the reaction, the reaction mixture was made alkaline by the addition of sodium carbonate, whereupon crystalline substances were separated in situ. The substances thus separated were recovered by filtration, washed with water and then recrystallized from 6 ml. of ethanol to give 0.1 g. of the pale yellow-colored pure desired product having a decomposition point of 125° C.

Analysis for $C_9H_{13}N_6O_2Cl$: Calculated: C, 39.64; H, 4.80; N, 30.82. Found: C, 39.64; H, 4.80; N, 30.42.

EXAMPLE 7

4-[3-(2-Chloroethyl)-3-nitrosoureido]-1-methylpiperidine

To a solution of 2 g. of 4-[3-(2-chloroethyl)ureido]-1-methylpiperidine in 10 ml. of 10% hydrochloric acid was added gradually 0.9 g. of sodium nitrite while stirring at 0° – 10° C. After completion of the addition, the resulting mixture was stirred at a temperature below 10° C. for additional 1 hour.

After completion of the reaction, the reaction mixture was made weakly alkaline to separate oily substance in situ. The reaction mixture was extracted with methylene chloride and the solvent was removed by distillation under reduced pressure to give the desired product as viscous oily substance. The substance was dissolved in 2 ml. of ethanol and then 2 ml. of 25% ethanolic hydrogen chloride added thereto. The resulting mixture was allowed to stand for a while, whereupon the pale-yellow colored hydrochloride of the desired product was separated out. The salt was recovered by filtration, washed with ethanol and then with ether, and dried to yield 0.5 g. of the desired product as pure hydrochloride having a decomposition point of 128° C.

Analysis for $C_9H_{18}N_4O_2Cl_2$: Calculated: C, 37.91; H, 6.36; N, 19.65. Found: C, 37.67; H, 6.51; N, 19.44.

EXAMPLE 8

4-[3-(2-Chloroethyl)-3-nitrosoureido]-2,2,6,6-tetramethylpiperidine

To a solution of 1 g. of 4-[3-(2-chloroethyl)ureido]-2,2,6,6-tetramethylpiperidine in 8 ml. of 10% hydrochloric acid was added gradually 0.4 g. of sodium nitrite at 0° – 5° C. After completion of the addition, the reaction mixture was stirred at a temperature below 10° C. for additional 1.5 hours. The crystalline substances separated out in situ during the stirring were recovered by filtration, washed with a small amount of cold water and recrystallized from aqueous methanol to give 0.5 g. of the pure hydrochloride.monohydrate of the desired product having pale yellow color and a decomposition point of 159° – 163° C.

Analysis for $C_{12}H_{26}N_4O_3Cl_2$: Calculated: C, 41.74; H, 7.59; N, 16.23. Found: C, 42.09; H, 7.68; N, 16.29.

EXAMPLE 9

1-{2-[3-(2-Chloroethyl)-3-nitrosoureido]ethyl}-cycloheptimidazole-2(1H)-one

To a solution of 0.3 g. of 1-{2-[3-(2-chloroethyl)-ureido]ethyl}cycloheptimidazole-2(1H)-one in 6 ml. of 2% hydrochloric acid was added portionwise 0.1 g. of sodium nitrite at 0° – 5° C. with stirring. After completion of the addition, the reaction mixture was stirred with ice-cooling for additional 1 hour.

After completion of the reaction, the reaction mixture was neutralized with sodium carbonate. The crystalline substances separated out in situ were recovered by filtration, washed with water and recrystallized from 50 ml. of ethanol to give 0.1 g. of the desired product as slightly yellowish prisms melting at 163° C. (with decomp.).

Analysis for $C_{13}H_{14}O_3N_5Cl$: Calculated: C, 48.23; H, 4.36; N, 21.63. Found: C, 48.28; H, 4.41; N, 21.51.

The product as obtained above (0.1 g.) was suspended in 4 ml. of ethanol and 0.5 ml. of 25% ethanolic hydrogen chloride was added thereto. The resulting mixture was stirred for a while. The crystalline substances formed in situ were recovered by filtration and recrystallized from 80% aqueous ethanol to give 50 mg. of the desired hydrochloride as slightly yellowish crystals melting at 182° C. (with decomp.)

Analysis for $C_{13}H_{15}O_3N_5Cl_2$: Calculated: C, 43.35; H, 4.20; N, 19.44. Found: C, 43.58; H, 3.86; N, 19.45.

EXAMPLE 10

1-{2-[3-(2-chloroethyl)-3-nitrosoureido]ethyl}-cycloheptimidazole-2(1H)-one-hydrochloride To a solution of 15 g. of 1-{2-[3-(2-chloroethyl)-ureido]ethyl}cycloheptimidazole-2(1H)-one in 90 ml. of 7% hydrochloric acid was added dropwise a solution of 5 g. of sodium nitrite in 10 ml. of water while stirring under ice-cooling. After completion of the dropwise addition, the reaction mixture was stirred at about 5° C. for additional 1 hours.

After completion of the reaction, the crystalline substances separated out in situ were recovered by filtration, washed with a small amount of cold water and then with methanol and recrystallized from 80% aqueous ethanol to give 8 g. of the desired hydrochloride as crystals melting at 182° C. (with decomp.)

EXAMPLE 11

6-Chloro-1{2-[3-(2-chloroethyl)-3-nitrosoureido]ethyl}cycloheptimidazole-2(1H)-one To a solution of 430 mg. of 6-chloro-1-{2-[3-(2-chloroethyl)ureido]ethyl}cycloheptimidazole-2(1H)-one in 2.5 ml. of 10% hydrochloric acid was added dropwise a solution of 270 mg. of sodium nitrite in 1 ml. of water while stirring under ice-cooling. The reaction mixture was stirred under ice-cooling for additional 2.5 hours.

After completion of the reaction, the reaction mixture was made alkaline by the addition of sodium carbonate. The crystalline substances separated out in situ were recovered by filtration and washed with water. The crude crystals thus obtained was dissolved in 6 ml. of dimethyl sulfoxide with heating. The resulting solution was filtered and the filtrate was diluted with 6 ml. of ethanol, thereby separating the desired product, which was then recovered by filtration, washed with ethanol and then dried to give 200 mg. of the pure desired product as slightly yellowish crystals melting at 190° C. (with decomp.).

Analysis for $C_{13}H_{13}N_5O_3Cl_2$: Calculated: C, 43.63; H, 3.72; N, 18.91. Found: C, 43.59; H, 3.66; N, 19.55.

EXAMPLE 12

5-Isopropyl-1-{2-[3-(2-chloroethyl)-3-nitrosoureido]ethyl}cycloheptimidazole-2(1H)-one hydrochloride To a solution of 0.4 g. of 5-isopropyl-1-{2-[3-(2-chloroethyl)ureido]-ethyl}cycloheptimidazole-2(1H)-one in 30 ml. of 10% hydrochloric acid was added dropwise a solution of 150 mg. of sodium nitrite in 0.5 ml. of water while stirring under ice-cooling. The resulting mixture was stirred under ice-cooling for additional 30 minutes.

After completion of the reaction, 10 ml. of water was added to the reaction mixture, insolubles were filered off, th filtrate was neutralized with an the aqueous solution of sodium carbonate and then extracted with chloroform. The extract was concentrated at room temperature, the residue worked with a small amount of 10% ethanolic hydrogen chloride and the product thus formed was recrystallized from ethanol to give 0.1 g. of the desired hydrochloride melting at 150° C. (with decomp.)

Analysis for $C_{16}H_{21}O_3N_5Cl_2$: Calculated: C, 47.83; H, 5.26; N, 17.41. Found: C, 48.21; H, 5.50; N, 17.17.

EXAMPLE 13

2-[3-(2-Chloroethyl)-3-nitrosoureido]methyl-1-methylbenzimidazole.hydrochloride.monohydrate To a solution of 200 mg. of 2-[3-(2-chloroethyl)-ureido]methyl-1-methylbenzimidazole in 2 ml. of 5% hydrochloric acid was added gradually 100 mg. of sodium nitrite while stirring under ice-cooling. The resulting mixture was stirred under ice-cooling for additional 2 hours. The colorless crystalline substances separated out in situ were recovered by filtration and the mother liquer was neutralized by the addition of sodium carbonate thereby separating crystalline substances, which were then recovered by filtration. Combined substances were recrystallized from ethanol to give 223 mg. of the desired product melting at 135° – 137° C. (with decomp.)

Analysis for $C_{12}H_{14}N_5O_2Cl.HCl.1H_2O$: Calculated: C, 41.16; H, 4.90; N, 20.00. Found: C, 40.90; H, 4.83; N, 20.04.

EXAMPLE 14

1-{2-[3-(2-Chloroethyl)-3-nitrosoureido]ethyl}-benzimidazole hydrochloride

To a solution of 1.45 g. of 1-{2-[3-(2-chloroethyl)-ureido]ethyl}benzimidazole in 10 ml. of water and 7.5 ml. of 10% hydrochloric acid was added gradually 800 mg. of sodium nitrite while stirring under ice-cooling. The resulting mixture was stirred under ice-cooling for additional 2 hours. Yellow crystalline substances separated out in situ (1.44 g.) was dissolved in 40 ml. of water and made alkaline with sodium carbonate. The alkaline mixture was extracted with 30 ml. portions (X2) and 10 ml. portions (X2) of chloroform. The combined chloroform extracts were dried and concentrated under reduced pressure. The residue was taken into 6 ml. of ethanol and, subsequently to the addition of 3 ml. of 30% ethanolic hydrogen chloride, 10 ml. of ether was added thereto at room temperature. The resulting mixture was allowed to stand in a cold place and the colorless crystalline substances separated were recovered by filtration and then recrystallized from methanol to give 578 mg. of the desired product melting at 173° – 174° C. (with decomp.)

Analysis for $C_{12}H_{14}N_5O_2Cl.HCl$: Calculated: C, 43.38; H, 4.55; N, 21.08. Found: C, 43.53; H, 4.65; N, 20.84.

EXAMPLE 15

1-{2-[3-(2-Chloroethyl)-3-nitrosoureido]propyl}-benzimidazole-hydrochloride

To a solution of 3.81 g. of 1-{2-[3-(2-chloroethyl)-ureido]propyl}benzimidazole in 20 ml. of water and 15 ml. of 10% hydrochloric acid was added gradually 1.9 g. of sodium nitrite while stirring under ice-cooling. The resulting mixture was stirred under ice-cooling for additional 2 hours.

After completion of the reaction, the yellow crystalline substances (3.25 g.) separated were recovered by filtration and dissolved in 100 ml. of water. The resulting solution was made alkaline by the addition of sodium carbonate and extracted with 40 ml. portions (X2) and 20 ml. portions (X2) of chloroform. The combined chloroform extracts were dried and concentrated under reduced pressure. The residue was taken into 10 ml. of ethanol and, subsequently to the addition of 5 ml. of 30% ethanolic hydrogen chloride, 15 ml. of ether was added thereto at room temperature. The resulting mixture was allowed to stand in a cold place. The pale yellow crystalline substances separated were recovered by filtration and then recrystallized from aqueous ethanol to give 2.36 g. of the desired product melting at 172° – 174° C. (with decomp.)

Analysis for $C_{13}H_{16}N_5O_2Cl.HCl$: Calculated: C, 45.09; H, 4.95; N, 20.23. Found: C, 45.23; H, 4.98; N, 20.28.

EXAMPLE 16

2-[3-(2-Chloroethyl)-3-nitrosoureidomethyl]-quinoline.hydrochloride.monohydrate

To a solution of 1.0 g. of 2-[3-(2-chloroethyl)-ureidomethyl]quinoline in 15 ml. of water and 5 ml. of 10% hydrochloric acid was added gradually 500 mg. of sodium nitrite while stirring in an ice bath. The resulting mixture was stirred under ice-cooling for additional 2 hours.

After completion of the reaction, the reaction mixture was made alkaline by the addition of sodium carbonate. The yellow oily substances separated were extracted with 15 ml. portions (X2) and then 10 ml. portions (X2) of chloroform. The combined chloroform extracts were dried and concentrated under reduced pressure to give 768 mg. of the free base as yellow oily substances.

The whole amount of the product as obtained above was dissolved in 5 ml. of ethanol and 350 mg. of 30% ethanolic hydrogen chloride was added thereto under ice-cooling. After 30 minutes, 3 ml. of ether was added to the mixture. After cooling, the pale yellow crystalline substances separated in situ were recovered by filtration and recrystallized from ethanol to give 633 mg. of the desired product melting at 139° – 140° C. (with decomp.)

Analysis for $C_{13}H_{13}N_4OCl.HCl.1H_2O$: Calculated: C, 47.17; H, 4.26; N, 16.93. Found: C, 47.29; H, 4.29; N, 17.03.

EXAMPLE 17

2-[3-(2-Chloroethyl)-3-nitrosoureido]methylthiazole hydrochloride

To a solution of 420 mg. of 2-[3-(2-chloroethyl)-ureido]methythiazole in 5 ml. of 5% hydrochloric acid was added gradually 250 ml. of sodium nitrite while stirring under ice-cooling. The resulting mixture was stirred under ice-cooling for additional 2 hours.

After completion of the reaction, the reaction mixture was neutralized and made alkaline by the addition of sodium carbonate and finally extracted with 10 ml. portions (X3) of chloroform. The combined chloroform extracts were dried and concentrated under reduced pressure to give 439 mg. of the free base as yellow oily substances.

The whole amount of the product as obtained above were dissolved in 1 ml. of ethanol and 0.7 ml. of 30% ethanolic hydrogen chloride was added dropwise with stirring at room temperature. After 30 minutes 2 ml. of ether was added to the mixture. The resulting mixture was allowed to stand in a cold place and the yellow crystalline substances separated were recovered by filtration and recrystallized from ethanol to give 332 mg. of the desired product melting at 122° – 123° C. (with decomp.)

Analysis for $C_7H_9O_2N_4SCl \cdot HCl$: Calculated: C, 29.48; H, 3.54; N, 19.65. Found: C, 29.85; H, 3.63; N, 19.60.

REFERENTIAL EXAMPLE 1

1-(2-Chloroethyl)-3-[(3-pyridyl)methyl]urea

To a solution of 2 g. of 3-aminomethylpyridine in 20 ml. of ether was added dropwise 1.65 ml. of 2-chloroethylisocyanate while stirring under ice-cooling. After completion of the dropwise-addition, the reaction mixture was stirred at room temperature for additional 30 minutes.

After completion of the reaction, the crystalline substance separated in situ was recovered by filtration and washed with ether to give 3 g. of the colorless desired product melting at 95° C.

Analysis for $C_9H_{12}N_3OCl$: Calculated: C, 50.59; H, 5.66; N, 19.67. Found: C, 50.35; H, 5.84; N, 19.68.

REFERENTIAL EXAMPLE 2

4-[3-(2-Chloroethyl)ureido]-1-methylpiperidine

To a solution of 2 g. of 4-amino-1-methylpiperidine in 30 ml. of ether was added dropwise under ice-cooling 1.6 ml. of 2-chloroethylisocyanate, during which colorless crystalline mass was being separated in situ. The reaction mixture was allowed to stand for additional 1 hours.

After completion of the reaction, the crystalline mass was recovered by filtration, washed with ether and dried to give 3.5 g. of the colorless desired product having a decomposition point of 125° – 130° C.

Analysis for $C_9H_{18}N_3OCl$: Calculated: C, 49.20; H, 8.26; N, 19.13. Found: C, 49.12; H, 7.94; N, 19.13.

REFERENTIAL EXAMPLE 3

1-{2-]3-(2-Chloroethyl)ureido]ethyl}cycloheptimidazole-2(1H)-one

To a solution of 26 g. of 1-(2-aminoethyl)cycloheptimidazole-2(1H)-one·dihydrochloride in 150 ml. of water was added a solution of 8 g. of sodium hydroxide in 50 ml. of water while stirring under ice-cooling. Then, 15 ml. of 2-chloroethyl isocyanate was added dropwise thereto over about 5 to 10 minutes. After completion of the dropwise addition, the reaction mixture was stirred for additional 15 minutes.

After completion of the reaction, the crystalline mass separated in situ was recovered by filtration and washed with water. Then, the mass was taken into a mixture of 200 ml. of water and 50 ml. of 10% hydrochloric acid and, after stirring for a while, insolubles were filtered off. The filtrate was treated with decoloring charcoal, neutralized with 10% aqueous sodium hydroxide and the crystalline substances separated was recovered by filtration and washed with water to give 17 g. of the desired product as slightly yellow needles melting at 170° C. (with decomp.)

Analysis for $C_{12}H_{15}O_2N_4Cl$: Calculated: C, 52.97; H, 5.13; N, 19.01. Found: C, 52.75; H, 5.20; N, 19.05.

What is claimed is:
1. 1-(2-Chloroethyl)-1-nitroso-3-[(2-methyl-4-aminopyrimidine-5-yl)methyl]urea.

* * * * *